(12) United States Patent
Abdelfattah et al.

(10) Patent No.: US 11,480,029 B2
(45) Date of Patent: Oct. 25, 2022

(54) AUTONOMOUS INFLOW CONTROL DEVICE FOR LIVE FLOW MONITORING

(71) Applicants: Tarik Abdelfattah, Houston, TX (US); Joshua Raymond Snitkoff, Houston, TX (US); Ian Mitchell, Katy, TX (US); Jose Rafael Gonzalez, Fulshear, TX (US); David Lerohl, Houston, TX (US); Roberto Failla, Cypress, TX (US)

(72) Inventors: Tarik Abdelfattah, Houston, TX (US); Joshua Raymond Snitkoff, Houston, TX (US); Ian Mitchell, Katy, TX (US); Jose Rafael Gonzalez, Fulshear, TX (US); David Lerohl, Houston, TX (US); Roberto Failla, Cypress, TX (US)

(73) Assignee: BAKER HUGHES OILFIELD OPERATIONS LLC, Houston, TX (US)

( * ) Notice: Subject to any disclaimer, the term of this patent is extended or adjusted under 35 U.S.C. 154(b) by 366 days.

(21) Appl. No.: 16/578,670

(22) Filed: Sep. 23, 2019

(65) Prior Publication Data

US 2021/0088476 A1     Mar. 25, 2021

(51) Int. Cl.
*E21B 34/06*     (2006.01)
*G01N 29/036*     (2006.01)
*G01N 29/24*     (2006.01)
*G01N 33/28*     (2006.01)
(Continued)

(52) U.S. Cl.
CPC ............. *E21B 34/06* (2013.01); *E21B 47/18* (2013.01); *E21B 49/08* (2013.01); *G01N 29/036* (2013.01); *G01N 29/2418* (2013.01); *G01N 33/2841* (2013.01); *G01N 33/2847* (2013.01); *E21B 49/0875* (2020.05)

(58) Field of Classification Search
CPC .......... E21B 34/06; E21B 47/18; E21B 49/08; E21B 34/08; E21B 49/0875; E21B 47/107; G01N 29/036; G01N 29/2418; G01N 33/2841; G01N 33/2847; G01N 2291/014; G01N 2291/02433; G01N 29/02; G01N 29/4436
See application file for complete search history.

(56) References Cited

U.S. PATENT DOCUMENTS

| 2002/0178805 A1 | 12/2002 | DiFoggio et al. |
| 2011/0122727 A1 | 5/2011 | Gleitman et al. |
| 2012/0072128 A1 | 3/2012 | Gao |

(Continued)

OTHER PUBLICATIONS

International Search Report and Written Opinion for PCT Application No. PCT/US2020/050841; dated Dec. 8, 2020; 11 pages.

*Primary Examiner* — Brad Harcourt
(74) *Attorney, Agent, or Firm* — Cantor Colburn LLP

(57) ABSTRACT

A production system and method of operating the production system. A fluid flows through a flow control device. The flow control device having an element that generates an acoustic signal indicative of a value of a parameter of the fluid in response to the fluid flowing through the flow control device. The processor receives the acoustic signal from the element, determines the value of the parameter of the fluid from the parameter of the acoustic signal, and changes an operation of the production system based on the value of the parameter of the fluid.

13 Claims, 7 Drawing Sheets

(51) Int. Cl.
*E21B 49/08* (2006.01)
*E21B 47/18* (2012.01)

(56) References Cited

U.S. PATENT DOCUMENTS

| | | | |
|---|---|---|---|
| 2012/0146805 A1* | 6/2012 | Vick, Jr. | E21B 34/14 |
| | | | 340/853.2 |
| 2013/0112406 A1 | 5/2013 | Zuo et al. | |
| 2014/0202240 A1* | 7/2014 | Skinner | E21B 47/107 |
| | | | 73/152.32 |
| 2015/0021015 A1 | 1/2015 | Xiao | |
| 2016/0245781 A1* | 8/2016 | Ahmad | E21B 47/107 |
| 2018/0217101 A1* | 8/2018 | Hopper | G01N 29/222 |
| 2019/0120048 A1* | 4/2019 | Coffin | E21B 47/07 |
| 2019/0212238 A1 | 7/2019 | Gao et al. | |

* cited by examiner

AUTONOMOUS INFLOW CONTROL DEVICE FOR LIVE FLOW MONITORING

BACKGROUND

In the resource recovery industry, a production string is placed into a wellbore during a completion operation in order to be able to produce formation fluids from a formation during a production operation. As the fluid is produced from the formation, several parameters of the fluid can change. In particular, the gas-oil ratio or gas volume fraction of the formation fluid changes during the production process. Operators generally wish to know the value of the gas-oil ratio in order to control production operations.

SUMMARY

In one embodiment, a method of operating a production system is disclosed. A fluid flows through a flow control device of the production system, the flow control device having an element that generates an acoustic signal indicative of a value of a parameter of the fluid. A processor measures the acoustic signal generated by the element, determines the value of the parameter of the fluid from the measured acoustic signal, and changes an operation of the production system based on the value of the parameter.

In another embodiment, a production system is disclosed. The production system includes a flow control device and a processor. The flow control includes an element that generates an acoustic signal in response to a fluid flowing through the flow control device, wherein a parameter of the acoustic signal is indicative of a value of a parameter of the fluid. The processor receives the acoustic signal from the element, determines the value of the parameter of the fluid from the parameter of the acoustic signal, and changes an operation of the production system based on the value of the parameter of the fluid.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method are presented herein by way of exemplification and not limitation with reference to the Figures.

Figure 1:
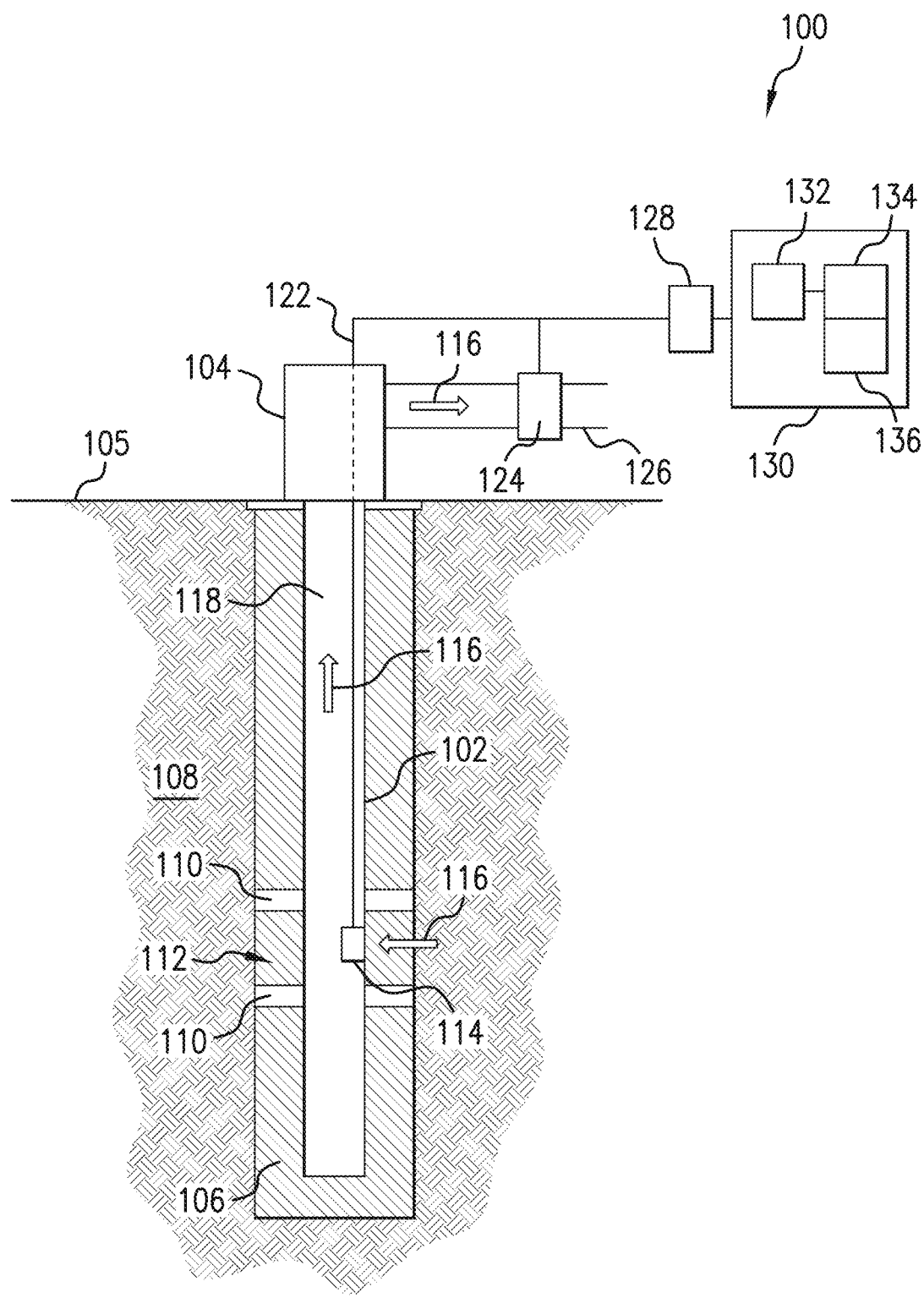
FIG. 1 shows an illustrative production system for directing fluid from a formation to a suitable surface location.

Referring to FIG. 1, an illustrative production system 100 for directing fluid from a formation 108 to a suitable surface storage location is disclosed. The production system 100 includes a production string 102 that extends from a production head 104 at a surface location 105 into a wellbore 106 penetrating the formation 108. The production string 102 includes one or more packers 110 that can be expanded to isolate a section 112 of the wellbore 106. A flow control device 114 is located on the production string within the isolated section 112. The flow control device 114 can be a fluid inlet device that controls a flow of a formation fluid 116 from the formation 108 into the production string 102. The formation fluid 116 flows into the production string 102 and uphole through an inner bore 118 of the production string 102 to the surface location 105.

The flow control device 114 is in communication with a control unit 130 via an optical interrogator. In various embodiments, optical signals are transmitted between the flow control device 114 and the control unit over a fiber optic cable 122. The optical interrogator propagates a signal through the fiber optic cable 122, measures properties of transmitted and reflected light and provides these light properties to the control unit 130. The control unit 130 includes a processor 132 and a memory storage device 134 having a set of instructions stored thereon which, when accessed by the processor 132, enables the processor to perform various functions at the production string. In various embodiments, the processor 132 can open or close a valve based on a measurements. Alternatively, the gas-oil ratio can be communicated to engineers and/or operators for gathering and interpreting the data to assess the flow profile of the well as well as to determine and action to be taken at the production system.

Although the flow control device 114 is shown as located at an inlet to the production string, this is only an illustrative embodiment. In other embodiments, the flow control device 114 can be located at other places in the production system 100, such as for example, along a surface pipe 126, as shown by flow control device 124.

Figure 2:
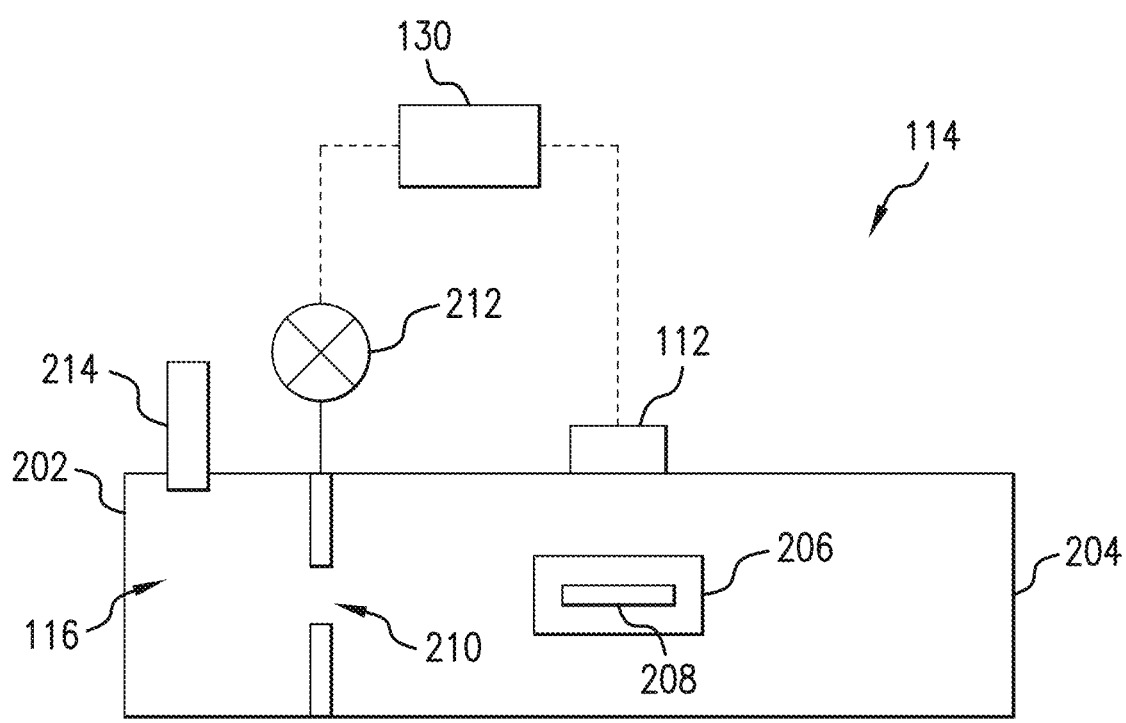
FIG. 2 shows a detailed diagram of the flow control device in an illustrative embodiment.

FIG. 2 shows a detailed diagram of the flow control device 114 in an illustrative embodiment. The flow control device 114 includes an inlet 202 for receiving a fluid such as the formation fluid 116 and an outlet 204 for egress of the fluid. The fluid control device 114 includes a sensor 206 that measures a parameter of the fluid passing through the fluid control device 114. The sensor 206 includes an element 208 that oscillates as fluid passes around it, thereby generating an acoustic signal. A parameter of the acoustic signal, such as the oscillation frequency of the element 208, is related to a parameter of the fluid, such as a gas-oil ratio of the fluid. In various embodiments, the element 208 oscillates at a first frequency when the gas-oil ratio is equal to a first value and the element 208 oscillates at a second frequency when the gas-oil ratio is equal to a second value. The control unit 130 measures the acoustic signal and/or frequency of oscillation of the element 208 and determines the gas-oil ratio of the fluid from the acoustic signal and/or frequency of oscillation. In addition, the control unit 130 can activate a device at the production system 100 to perform an action based on the gas-oil ratio of the fluid. For example, the control unit 130 can activate a valve 212 to either increase or reduce an aperture 210 of the flow control device 114, thereby increasing or reducing a fluid flow rate and/or the fluid intake at the flow control device 114. Also, the control unit 130 can operate a choke 214 to regulate a gas level in the fluid, for example, by reducing an amount of gas in the fluid. The parameter of the acoustic signal can also be indicated of a water/oil ratio as well as an oil/water/gas ratio.

In various embodiments, the fiber optic cable 122 is disposed at the flow control device 114. The fiber optic cable 122 is disposed at a location so as to be receptive to the acoustic signals propagating throughout the flow control device 114 due to oscillation of the element 208. The acoustic signals can be due to the oscillation of the element 208 but can also be due to noise generated by the fluid and/or gas flowing through the flow control device 114, such noises include, hammering, cavitation, choke wave effects, etc. The acoustic waves from the oscillating element 208 induce a fluctuation in a parameter of light propagating through the fiber optic cable. In various embodiments, the parameter of light can be an intensity of the light or a wavelength of the light, which can be achieved using Rayleigh scattering based Distributed Acoustic Sensing and/or Fiber Bragg gratings in the fiber optic cable 122. The fluctuations in the parameter of light is then measured at the processor in order to determine the parameters of the acoustic signal, such as the oscillation frequency of the element 208.

In various embodiments, the processor 132 can normalize the received signal to a reference signal (or reference frequency) in order to determine the gas-oil ratio. The reference signal can be a signal obtained at the flow control device during early production stages from the well. Alternatively, or subsequently, the reference signal can be a signal obtained from laboratory testing.

Figure 3:
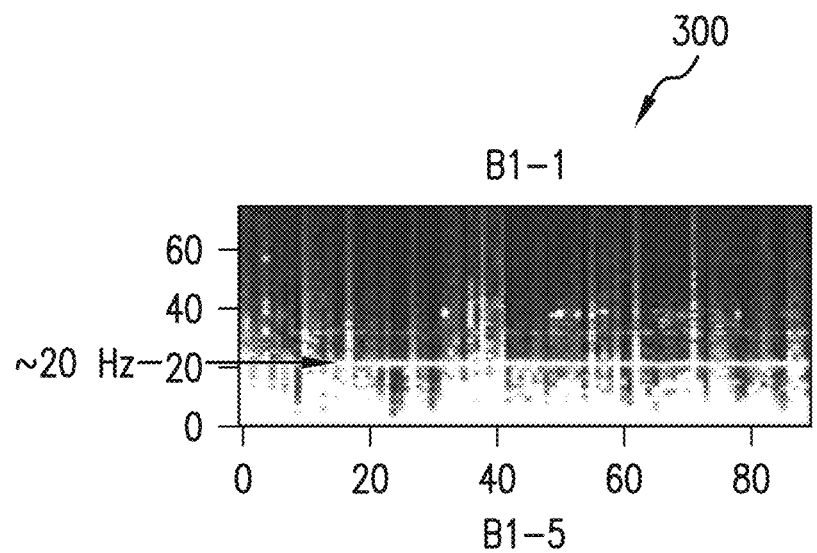
FIG. 3 shows a spectrogram received from a flow control device showing a frequency of oscillation for a fluid flowing through the flow control device.
Figure 4:
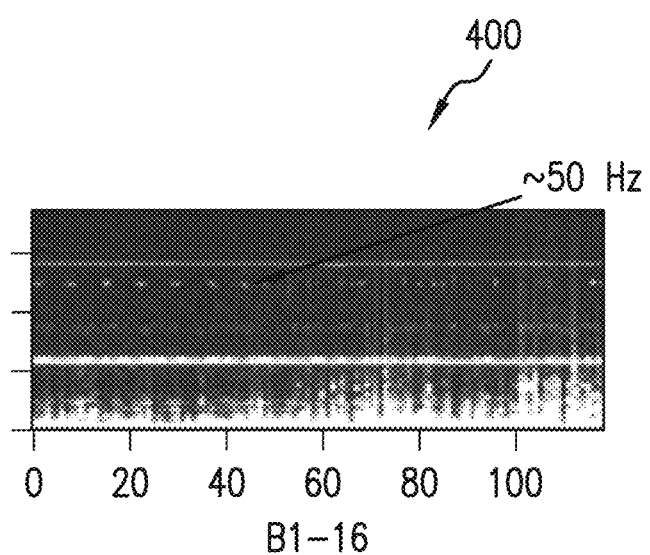
FIG. 4 shows another spectrogram shows a frequency of oscillation for a fluid that includes a gas.

FIG. 3 shows a spectrogram 300 received from a flow control device showing a frequency of oscillation associated with a fluid flowing through the flow control device. Time is shown along the x-axis and frequency is shown along the y-axis. A signal having a frequency of about 20 Hz is shown in FIG. 3, indicating a fluid having oil only. FIG. 4 shows another spectrogram 400 showing a frequency of oscillation for a fluid that includes a gas. Time is shown along the x-axis and frequency is shown along the y-axis. The appearance of an oscillation at about 50 Hz is shown. The oscillation at about 50 Hz indicates the presence of gas in the fluid.

Figure 5:
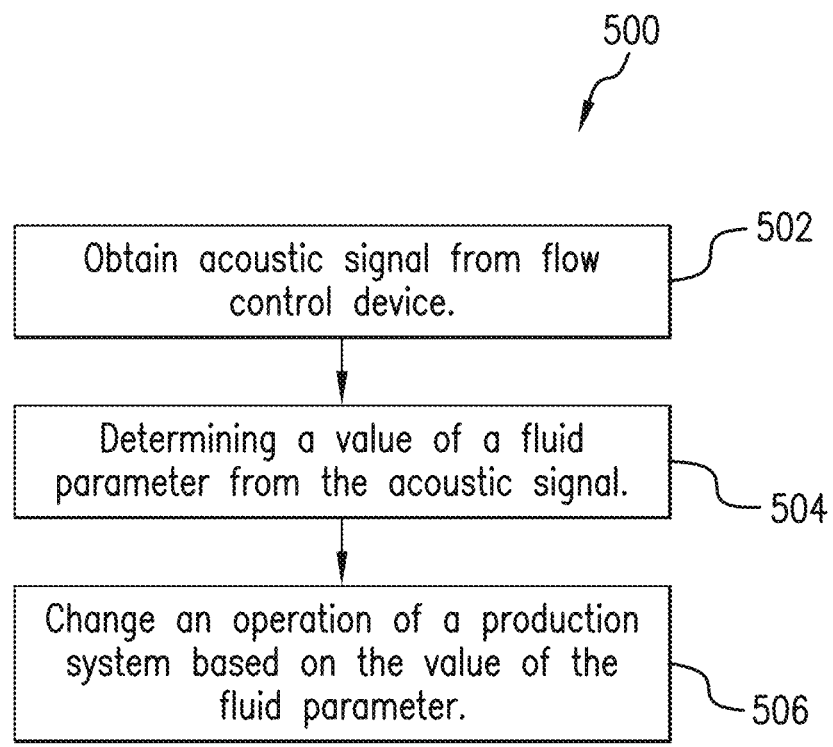
FIG. 5 shows a flowchart illustrating a method of operating a production system as disclosed herein.

FIG. 5 shows a flowchart 500 illustrating a method of operating a production system as disclosed herein. In box 502, acoustic signal is received from a flow control device. The acoustic signal can be from an element of the flow control device that oscillates due to flow of a fluid across the element and/or noises produced by fluid and/or gas flowing through the flow control device. In box 504, a value of a parameter of the fluid is determined from a parameter of the acoustic signal, such as an oscillation frequency. In box 506, the value of the parameter of the fluid is used to change an operation of the production system.

Figure 6:
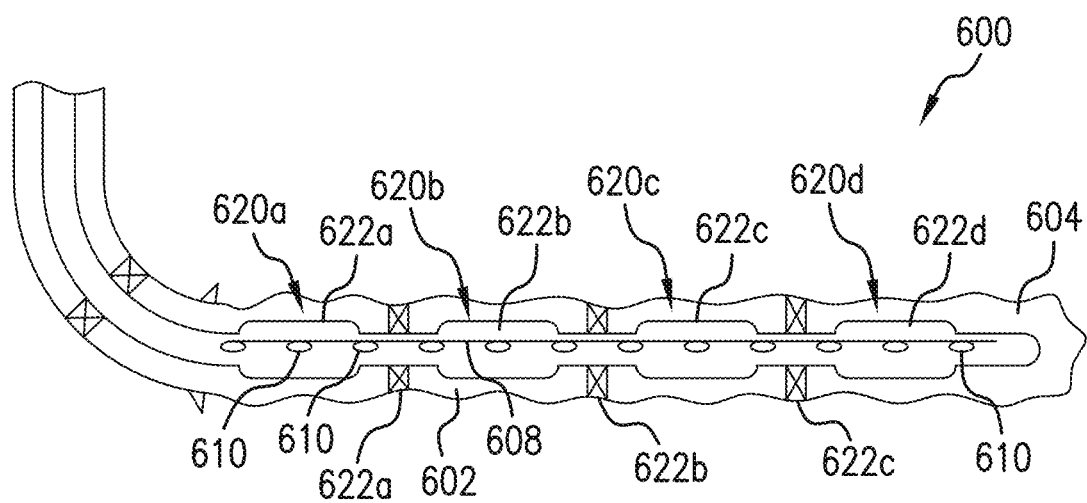
FIG. 6 shows a production string extending through a horizontal section of a wellbore.

FIG. 6 shows a production string 600 extending through a horizontal section 602 of a wellbore 604. The production string 600 includes a plurality of sensors 610 spaced apart along a fiber optic cable 608 extending along the length of the production string 600. The sensors 610 can be the sensors 206 discussed herein, in one embodiment. The sensors 610 can be spatially arranged on the fiber optic cable 608 to have a spatial resolution that extracts an acoustic signal indicative of the acoustic signal of a selected flow control device. Additionally, the sensors 610 provide enough temporal resolution that allows an operator to perform production optimization efforts if needed. Such effort can include shutting off a selected zone or stage, creating more pull using and artificial lift device, etc.

The horizontal section 602 includes an open hole wellbore that is partitioned into a plurality of stages 620a, 620b, 620c and 620d via a plurality of isolation packers 622a, 622b, 622c on the production string 600. Each stage 620a, 620b, 620c, 620d includes a respective screens 624a, 624b, 624c, 624d, and valves or flow control devices for controlling fluid flow of formation fluid into their respective stages 620a, 620b, 620c, 620d of the production string 600. Each stage 620a, 620b, 620c, 610d includes at least one of the sensors 610. Each sensor 610 determines a gas-oil ratio or gas volume fraction at the location of the sensor, which can be used to control a flow control device associated with the sensor. Each sensor 610 can provides its measurement to a processor along with an associated depth of the sensors. 610.

Figure 7A:
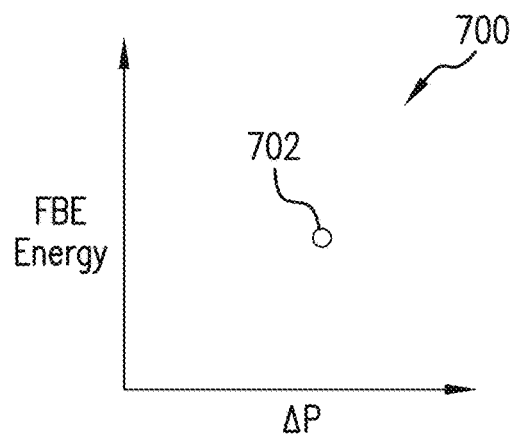
FIGS. 7A-7C shows graphs illustrating a process that can be used to determine a profile of gas volume fraction and to control fluid production operations.
Figure 7B:
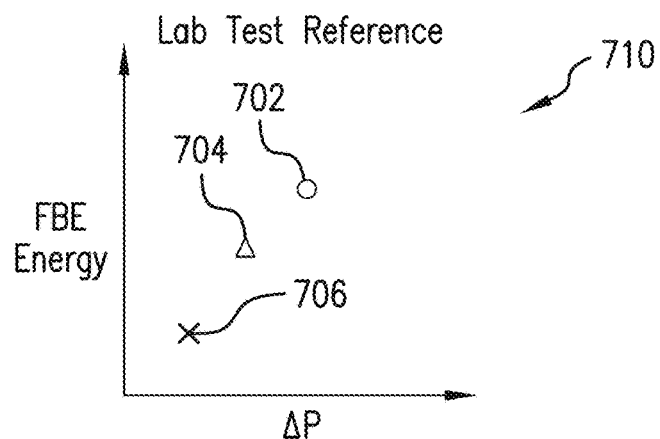
Figure 7C:
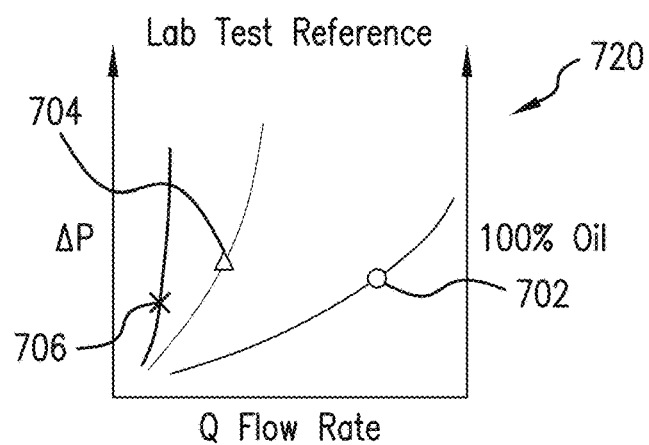

FIGS. 7A-7C shows graphs illustrating a process that can be used to determine a profile of gas volume fraction and to control fluid production operations. FIG. 7A shows a graph 700 having a pressure measurement 702 obtained from a sensor. Frequency band extracted energy is shown along a y-axis and pressure difference is shown along the x-axis. The graph 700 shows a peak in a frequency band extracted energy at a selected differential pressure. FIG. 7B shows a graph 710 of peak extracted energy to differential pressure which includes pressure measurements obtained from a plurality of sensors 610 along the production string 600. FIG. 7B is data obtained through lab testing as well as the data obtained from downhole. The data obtained downhole is matched up against the lab data in order to identify the level of energy downhole. FIG. 7B shows the pressure measurement 702 from FIG. 7A and two additional pressure measurements 704 and 706 obtained from different sensors. Each measurement can be identified to its related sensor and position along the production string 600.

FIG. 7C shows a graph 720 of a relation between pressure drop and flow rate at a sensor. The pressure measurements 702, 704, 706 from FIG. 7B are compared to laboratory results in order to determine the flow rates associate with the pressure measurements. These flow rates are then plotted against pressure differential as shown in FIG. 7C. Gas volume ratio lines can be introduced into the graph 720 in order to identify the gas volume ratio that corresponds to the pressure measurement. For example, measurement 702 has a volume fraction of 100% oil, measurement 704 has volume fractions of 25% oil and 75% gas, and measurement 706 has a volume fraction of 100% gas. This method therefore can be used to determine flow rate as well as gas volume fraction from a pressure measurement at a sensor.

Figure 8:
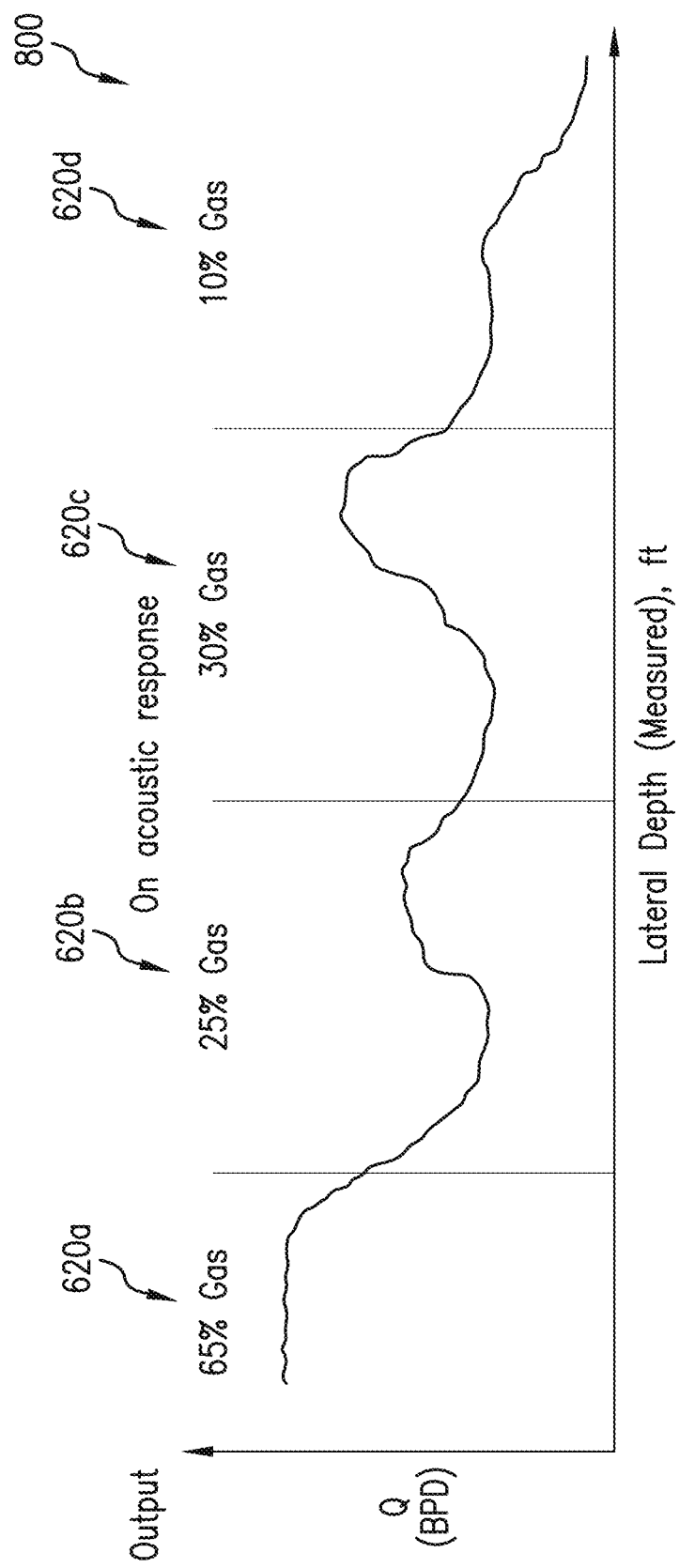
FIG. 8 shows a graph showing a relation of flow rate to depth for fluid extracted from various depths of the wellbore.

FIG. 8 shows a graph 800 showing a relation of flow rate to depth for fluid extracted from various depths of the wellbore. The graph 800 can be partitioned along the depth axis according to the stages 620a, 620b, 620c, 620d of the wellbore, in order to indicate the gas or water volume fraction for each stage. An operator can determine the gas or water volume fraction from the graph 800 at each stage and determine an operation regarding the wellbore based on the gas volume fraction, such as selecting to open or close valves within a selected stage in order to produce fluid having a selected gas or water volume fraction, for example.

Set forth below are some embodiments of the foregoing disclosure:

Embodiment 1: A method of operating a production system. The method includes: flowing a fluid through a flow control device of the production system, the flow control device having an element that generates an acoustic signal indicative of a value of a parameter of the fluid; measuring, at a processor, the acoustic signal generated by the element; determining, at a processor, the value of the parameter of the fluid from the measured acoustic signal; and changing an operation of the production system based on the value of the parameter.

Embodiment 2: The method of any prior embodiment, wherein the parameter is one of: (i) a gas/oil ratio of the fluid; (ii) a water/oil ratio; and (iii) an oil/water/gas ratio.

Embodiment 3: The method of any prior embodiment, wherein the value of the parameter is related to a frequency of oscillation of the element, the method further comprising measuring the frequency of oscillation indicated by the acoustic signal and determining the value of the parameter of the fluid from the measured frequency of oscillation.

Embodiment 4: The method of any prior embodiment, further comprising measuring the acoustic signal by measuring an optical signal sensitive to the acoustic signal.

Embodiment 5: The method of any prior embodiment, wherein the optical signal propagates through an optical fiber disposed along a section of the flow control device.

Embodiment 6: The method of any prior embodiment, further comprising comparing the acoustic signal to a reference signal in order to determine the value of the parameter of the fluid.

Embodiment 7: The method of any prior embodiment, wherein the reference signal is at least one of: (i) a signal received during an early production flow from the well; and (ii) a signal determined from lab testing.

Embodiment 8: The method of any prior embodiment, wherein changing the operation of the production system further comprises at least one of: (i) change a flow rate of the fluid; and (ii) changing a choke setting at the production system.

Embodiment 9: A production system. The production system includes a flow control device; an element of the flow control device that generates an acoustic signal in response to a fluid flowing through the flow control device, a parameter of the acoustic signal being indicative of a value of a parameter of the fluid; and a processor. The processor is configured to: receive the acoustic signal from the element; determine the value of the parameter of the fluid from the parameter of the acoustic signal; and change an operation of the production system based on the value of the parameter of the fluid.

Embodiment 10: The production system of any prior embodiment, wherein the parameter of the fluid is one of: (i) a gas-oil ratio of the fluid; (ii) a water/oil ratio; and (iii) an oil/water/gas ratio.

Embodiment 11: The production system of any prior embodiment, wherein the parameter of the acoustic signal is a frequency of oscillation of the element, the processor being further configured to measure the frequency of oscillation from the acoustic signal and determine the value of the parameter of the fluid from the measured frequency of oscillation.

Embodiment 12: The production system of any prior embodiment, further comprising an optical fiber having an optical signal propagated therein, the optical signal being sensitive to the acoustic signal.

Embodiment 13: The production system of any prior embodiment, wherein the optical fiber is disposed along a section of the flow control device.

Embodiment 14: The production system of any prior embodiment, wherein the processor is further configured to compare the acoustic signal to a reference signal in order to determine the value of the parameter of the fluid.

Embodiment 15: The production system of any prior embodiment, wherein the processor is further configured to change the operation of the production system by changing at least one of: (i) a flow rate of the fluid; and (ii) a choke setting at the production system.

The use of the terms "a" and "an" and "the" and similar referents in the context of describing the invention (especially in the context of the following claims) are to be construed to cover both the singular and the plural, unless otherwise indicated herein or clearly contradicted by context. Further, it should be noted that the terms "first," "second," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

The teachings of the present disclosure may be used in a variety of well operations. These operations may involve using one or more treatment agents to treat a formation, the fluids resident in a formation, a wellbore, and/or equipment in the wellbore, such as production tubing. The treatment agents may be in the form of liquids, gases, solids, semi-solids, and mixtures thereof. Illustrative treatment agents include, but are not limited to, fracturing fluids, acids, steam, water, brine, anti-corrosion agents, cement, permeability modifiers, drilling muds, emulsifiers, demulsifiers, tracers, flow improvers etc. Illustrative well operations include, but are not limited to, hydraulic fracturing, stimulation, tracer injection, cleaning, acidizing, steam injection, water flooding, cementing, etc.

While the invention has been described with reference to an exemplary embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited.

What is claimed is:

1. A method of operating a production system, comprising:

flowing a fluid through a flow control device of the production system, the flow control device having an element that oscillates when the fluid flows around the element to generate an acoustic signal, wherein a frequency of the acoustic signal is indicative of a value of a gas-volume fraction of the fluid;

inducing a fluctuation in a light signal propagating through a fiber optic cable disposed at the flow control device to generate a light frequency related to the frequency of the acoustic signal;

measuring, at a processor, the frequency of the reflected light;

determining, at the processor, the value of the gas-volume fraction of the fluid from the measured frequency of the reflected light; and changing an operation of the production system based on the value of the gas-volume fraction.

2. The method of claim 1, further comprising determining one of: (i) a gas/oil ratio of the fluid; (ii) a water/oil ratio; and (iii) an oil/water/gas ratio.

3. The method of claim 1, further comprising measuring the frequency of the acoustic signal by measuring an optical signal sensitive to the acoustic signal.

4. The method of claim 3, wherein the optical signal propagates through an optical fiber disposed along a section of the flow control device.

5. The method of claim 1, further comprising comparing the frequency of the acoustic signal to a frequency of a reference signal in order to determine the value of the gas-volume fraction of the fluid.

6. The method of claim 5, wherein the reference signal is at least one of: (i) a signal received during an early production flow from the well; and (ii) a signal determined from lab testing.

7. The method of claim 1, wherein changing the operation of the production system further comprises at least one of: (i) change a flow rate of the fluid; and (ii) changing a choke setting at the production system.

8. A production system, comprising:
a flow control device;
an element of the flow control device that generates an acoustic signal in response to a fluid flowing through the flow control device and around the element, a frequency of the acoustic signal being indicative of a value of a gas-volume fraction of the fluid; and
a fiber optic cable disposed at the flow control device, wherein the acoustic signal induces a fluctuation in a light signal propagating through a fiber optic cable to generate a light frequency related to the frequency of the acoustic signal;
a processor configured to:
receive the frequency of the reflected light;
determine the value of the gas-volume fraction of the fluid from the frequency of the reflected light; and
change an operation of the production system based on the value of the gas-volume fraction of the fluid.

9. The production system of claim 8, wherein the processor is further configured to determine one of: (i) a gas-oil ratio of the fluid; (ii) a water/oil ratio; and (iii) an oil/water/gas ratio.

10. The production system of claim 8, further comprising an optical fiber having an optical signal propagated therein, the optical signal being sensitive to the acoustic signal.

11. The production system of claim 10, wherein the optical fiber is disposed along a section of the flow control device.

12. The production system of claim 8, wherein the processor is further configured to compare the frequency of the acoustic signal to a frequency of a reference signal in order to determine the value of the parameter of the fluid.

13. The production system of claim 8, wherein the processor is further configured to change the operation of the production system by changing at least one of: (i) a flow rate of the fluid; and (ii) a choke setting at the production system.

* * * * *